United States Patent [19]

Norris

[11] Patent Number: 5,157,201

[45] Date of Patent: Oct. 20, 1992

[54] PROCESS FOR ADSORBING SULFUR SPECIES FROM PROPYLENE/PROPANE USING REGENERABLE ADSORBENT

[75] Inventor: Donald J. Norris, Clearwater, Canada

[73] Assignee: Exxon Chemical Patents Inc., Linden, N.J.

[21] Appl. No.: 542,289

[22] Filed: Jun. 22, 1990

[51] Int. Cl.⁵ .............................................. C10G 35/00
[52] U.S. Cl. ..................................... 585/820; 585/823; 208/208 R; 208/243; 208/244; 208/245; 208/247; 208/250
[58] Field of Search .......................... 585/820, 823; 208/208 R, 243, 244, 245, 250

[56] References Cited

U.S. PATENT DOCUMENTS

| | | | |
|---|---|---|---|
| 2,362,296 | 11/1944 | Murphree et al. | 208/250 |
| 2,618,586 | 11/1952 | Hendel | 208/250 |
| 2,760,908 | 8/1956 | Clines | 208/250 |
| 2,771,465 | 11/1956 | Whitney | 585/823 |
| 2,959,538 | 11/1960 | Weikart et al. | 208/211 |
| 2,971,824 | 2/1961 | Johnson et al. | 583/823 |
| 3,051,646 | 8/1962 | Brooke | 585/823 |
| 3,188,293 | 6/1965 | Bacon et al. | 208/250 |
| 3,233,003 | 2/1966 | Epperly et al. | 585/823 |
| 3,660,276 | 3/1969 | Lacey | 208/212 |
| 3,778,486 | 12/1973 | Hamby, Jr. | 585/823 |
| 4,088,736 | 5/1978 | Courty et al. | 423/210 |
| 4,098,684 | 7/1978 | Innes | 585/823 |
| 4,300,999 | 11/1981 | Davies et al. | 208/212 |
| 4,313,820 | 2/1982 | Farha, Jr. et al. | 208/213 |
| 4,533,529 | 8/1985 | Lee | 423/230 |
| 4,540,842 | 9/1985 | Allen | 585/823 |
| 4,571,445 | 2/1986 | Slaugh | 585/853 |
| 4,795,545 | 11/1984 | Schmidt | 585/823 |
| 4,835,338 | 5/1989 | Lin | 585/823 |

FOREIGN PATENT DOCUMENTS

| | | | |
|---|---|---|---|
| 1,742,326 | 5/1970 | Belgium | 585/823 |
| 1142339 | 2/1969 | Fed. Rep. of Germany . | |

OTHER PUBLICATIONS

"Hydrodesulphurization Activity and Coking Propensity of Carbon and Alumina Supported Catalyst", Vincentius H. F. de Beer et al., presented at the conference "Carbons and Catalysis" held in London, Dec. 19-20, 1983.

*Primary Examiner*—Helane E. Myers
*Attorney, Agent, or Firm*—Edward F. Sherer

[57] ABSTRACT

A method of removing sulfur components from a hydrocarbon stream which involves contacting a hydrocarbon stream including an initial amount of at least one sulfur species selected from the group consisting of mercaptans, organic sulfides, and disulfides with a catalyst capable of adsorbing the surfur species in the absence of extraneously added hydrogen and under conditions suitable for removing the at least one sulfur species from the hydrocarbon stream by the catalyst to form a resultant hydrocarbon stream containing a reduced amount of the at least one sulfur species.

30 Claims, 2 Drawing Sheets

PROCESS FOR ADSORBING SULFUR SPECIES FROM PROPYLENE/PROPANE USING REGENERABLE ADSORBENT

BACKGROUND OF THE INVENTION

1. Field of the Invention

The present invention relates to removing sulfur species from a hydrocarbon stream, and is specifically directed to a method of removing sulfur components selected from the group consisting of mercaptans, organic sulfides and disulfides from a hydrocarbon stream in the absence of extraneously added hydrogen.

More specifically, the present invention is directed to a process for adsorbing sulfur species, i.e., disulfides, organic sulfides and mercaptans, from an olefinic hydrocarbon stream, e.g., containing propylene and propane, by contacting the hydrocarbon stream with a catalyst capable of adsorbing the sulfur species, i.e., one which preferably contains metal oxides selected from the group consisting of a mixture of cobalt and molybdenum oxides, a mixture of nickel and molybdenum oxides, or nickel oxide, in the absence of extraneously added hydrogen and under conditions suitable for adsorbing the sulfur species from the hydrocarbon stream, i.e., a temperature within the range of about 75° C.–175° C., but preferably about 75° C.; a pressure within the range of 150 psig–1100 psig, but preferably about 175 psig; and a liquid hourly space velocity within the range of about 0.5 v/v/h–10 v/v/h, but preferably about 1 v/v/h to form a resultant hydrocarbon stream containing a reduced amount of the sulfur species, i.e. less than about 20% by weight, relative to the initial content of the sulfur species in the hydrocarbon feedstream.

2. Discussion of Background and Material Information

In the petroleum industry, higher olefin plants typically use a propylene feedstock containing various amounts of propylene, propane, butylenes and butanes, and commonly a mixture of 50% propylene and 50% propane. The typical propylene feedstock normally contains from about 5-50 ppm of various sulfur species. Dimethyl sulfides, methyl ethylsulfides, diethyl sulfides, dimethyl disulfide, methyl mercaptan and ethylmercaptan are the most typical of the sulfur species present in these feedstreams.

During oligomerization, however, the sulfur species tend to become incorporated in the higher olefins. Although higher olefins containing sulfur can be used as feedstock for various chemical processes, the sulfur in the higher olefin hydrocarbon streams typically contribute to the production of resultant product streams which are lower in quality than if sulfur were not present in, or removed from, the olefinic hydrocarbon feedstream.

Prior to the present invention, attempts have been to desulfurize higher olefin products over a sacrificial nickel catalyst; however, such processes also suffer from numerous disadvantages.

A typical example of a known desulfurizing technique which has been proposed for this purpose involves subjecting dimethyl sulfide (DMS) and dimethyl disulfide (DMDS) to a sulfided conventional hydrodesulfurization catalyst, such as cobalt-molybdenum (CoMo) or nickel-molybdenum (NiMo) on alumina. In such a catalyst sulfiding, inactive metal oxides are converted to metal sulfides as described hereinafter. A stream of naphtha or gas oil containing 6,000–20,000 wppm DMS or DMDS is mixed with a stream of hydrogen gas and heated to a temperature within the range of 200° C. to 300° C. As the mixture is passed over the catalyst, in its metal oxide form, the sulfur species are thermally and catalytically decomposed by the hydrogen to produce hydrogen sulfide and methane as follows: $CH_3-S-CH_3+H_2 > 2CH_4+H_2S$; hydrogen sulfide reacts with metal oxides in the catalyst to form the corresponding sulfides:

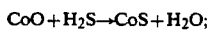

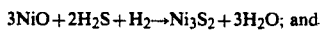

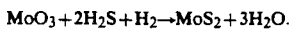

These metal sulfide catalysts are conventionally used with hydrogen to catalytically convert sulfur in hydrocarbon feedstocks to hydrogen sulfide, thus allowing the sulfur to be removed by simple stripping.

A similar process using hydrogen cannot be used to hydrodesulfurize propylene as these catalysts are well known to catalyze hydrogenation of alkenes. Although not wishing to be bound to any particular theory, it is believed that hydrodesulfurization, using metal sulfide catalysts, would hydrogenate propylene to undesirable propane in combination with or even preferentially over, sulfur removal.

U.S. Pat. No. 2,959,538, WEIKART et al., is directed to a process for hydrodesulfurizing petroleum oil feed containing naphtha, kerosene, and diesel oil fractions which involves passing hydrofined products through a zinc oxide drum which is at a pressure of 200 psig so as to convert the hydrogen sulfide present as a result of the hydrofining to $H_2O$ and zinc sulfide before passing the desulfurized hydrocarbon and hydrogen vapors and gases to a fractionator.

U.S. Pat. No. 3,063,936, PEARCE, relates to desulfurization of hydrocarbon oils, which are intended to be used for the manufacture of methanol from a mixture of carbon monoxide and hydrogen produced by steam reforming of a straight-run naphtha. The desulfurization occurs in three stages including one wherein vaporized hydrocarbon oil is passed over a contact material comprising zinc oxide, manganese oxide or iron oxide, but preferably zinc oxide, at a temperature between about 350° C. and 450° C., and at a pressure between about 1 and 50 atmospheres, prior to passing the vaporized hydrocarbon, together with hydrogen, at a temperature between 350° C. and 450° C., and at a pressure between about 1 and 50 atmospheres, over a hydrodesulfurization catalyst, followed by contacting the resultant product with a hydrogen sulfide absorbing catalyst. It is disclosed that the contact material comprises zinc oxide, manganese oxide or iron oxide, with zinc oxide being preferred. The hydrodesulfurization catalysts are disclosed as being selected from the group of palladium, platinum or cobalt molybdate, supported on alumina wherein the cobalt molybdate are composed of oxides of cobalt and molybdenum. It is disclosed that any suitable material which is capable of absorbing hydrogen sulfide may be used in the third stage of the process but that absorbing material preferably includes zinc oxide, manganese oxide or iron oxide with zinc oxide is preferred.

U.S. Pat. No. 3,660,276, LACEY, is directed to a process for desulfurizing hydrocarbon distillate oils wherein a mixture of the oil vapor in the carbon dioxide-containing hydrogenating gas is passed over a hydrodesulfurization catalyst and then over a material capable of absorbing hydrogen sulfide and eliminating any carbonyl sulfide present either by absorbing the carbonyl sulfide or by converting it to hydrogen sulfide and absorbing the hydrogen sulfide. It is disclosed that the hydrodesulfurization catalyst may contain molybdenum or nickel or cobalt with a preferred catalyst containing molybdenum which is promoted by the presence of nickel and supported on alumina. Another disclosed example of hydrodesulfurization catalysts is molybdenum coated with cobalt and supported on alumina. Materials which are disclosed as being capable of quantitatively absorbing hydrogen sulfide and also eliminating carbonyl sulfides is zinc oxide, with zinc oxide-copper oxide compositions being disclosed as an alternative.

U.S. Pat. No. 4,088,736, COURTY, is directed to a process for purifying a hydrogen sulfide-containing gas which involves absorbing the hydrogen sulfide onto a mass composed of zinc oxide, alumina, and a Group IIA metal oxide, wherein a large proportion of the Group IIA metal oxide is in the form of aluminate or silicoaluminate. The solid contact materials disclosed as being useful for this purpose are described as being thermally stable and regenerable and contain, by weight, 20-85% of zinc oxide, 0.9-50% of alumina, and 2-45% of oxide of a Group IIA metal with or without additional elements which may be 0.1-30% by weight silica, or one or several oxides of a metal selected from the group consisting of copper, cadmium, titanium, zirconium, vanadium, chromium, molybdenum, tungsten, manganese, iron, cobalt, and nickel wherein the latter oxides are disclosed as making the absorption of $H_2S$, COS, $CS_2$ and the regeneration of the absorption material easier.

U.S. Pat. No. 4,300,999, relates to gas oil purification wherein hydrogen sulfide is absorbed by passing partially vaporized oil, hydrogen-containing gas and hydrogen over zinc oxide, wherein the organic sulfur compounds which are removed are disclosed as being carbonyl sulfides (COS) and carbon disulfide ($CS_2$).

U.S. Pat. No. 4,313,820, FARHA, is directed to the removal of hydrogen sulfide from a fluid stream by contacting the fluid stream which contains hydrogen sulfide with an absorbing composition which is composed of zinc, titanium and at least one promoter selected from the group consisting of vanadium, chromium, manganese, iron, cobalt, nickel, molybdenum, rhenium, and compounds thereof. It is disclosed that if organic sulfur compounds are present in the fluid stream, the absorbing composition acts as a hydrodesulfurization catalyst to convert the sulfur in the organic sulfur compounds to hydrogen sulfide which is subsequently removed from the fluid stream by the absorbing composition. If olefin contaminants are present in the fluid stream, the absorbing composition acts as a hydrogenation catalyst to hydrogenate the olefin contaminants to paraffins.

U.S. Pat. No. 4,533,529, LEE, is directed to the removal of sulfur species from a Claus plant tail gas stream by contacting with zinc oxide in the presence of sufficient reducing equivalents for conversion of sulfur compounds to hydrogen sulfide; alternatively, the sulfur compounds are converted to hydrogen sulfide prior to contacting with the zinc oxide.

U.S. Pat. No. 4,571,445, SLAUGH, is directed to reducing the level of sulfur compounds from liquid conjugated diolefin hydrocarbons by contacting the sulfur compound-bearing hydrocarbon liquids with sorbents prepared by combining particulate alumina with at least one compound decomposable to sodium oxide, barium oxide, calcium oxide, or a salt decomposable to potassium oxide.

U.S. Pat. No. 4,593,148, JOHNSON, is directed to the removal of hydrogen sulfide from gaseous streams by contacting the gas streams with a sorbent material which is composed of copper oxide and zinc oxide, preferably wherein the absorbent material is prepared by coprecipitating hydroxides of copper and zinc, and subsequently heating the hydroxides so as to convert the hydroxides to CuO ZnO with aluminum oxide being disclosed as being an optional component of the sorbent material.

GB 1,142,339, BADISCHE ANILIN & SODA-FABRIK AKTIENGESELLSCHAFT, is directed to the removal of carbonyl sulfide from gas mixtures using metal oxides.

SUMMARY OF THE INVENTION

In accordance with the present invention, therefore, metal oxides are used to adsorb sulfur species, i.e., mercaptans, organic sulfides, and disulfides, from an olefin stream, such as propylene/propane stream, without using hydrogen to promote decomposition of the sulfur species and thereby avoiding hydrogenation of propylene to undesirable propane.

The process of the present invention involves supplying adsorbent particles, either unsupported metal oxides, or metal oxides on an inert support, to one or more vessels as an adsorbent bed. A stream of propylene/propane containing about 5-100 wppm of sulfur, as various species, but preferably selected from the group consisting of mercaptans, organic sulfides, and disulfides, is then heated or cooled as necessary and passed through the adsorbent bed or beds. Typical operating conditions are: temperatures within the range of about 50° C.-175° C.; pressures within the range about 150 psig-1100 psig; and Liquid Hourly Space Velocities within the range of about 0.5 v/v/h-10 v/v/h. The treated substantially sulfur-free propylene/propane may then be fed into conventional higher olefin processes. The deactivated adsorbent may be regenerated.

More generally speaking, however, the method for removing sulfur components from a hydrocarbon stream involves contacting a hydrocarbon stream including at least one sulfur species selected from the group consisting of mercaptans, organic sulfides, and disulfides with a catalyst capable of adsorbing the sulfur species in the absence of extraneously added hydrogen under conditions suitable for adsorbing the sulfur species from the hydrocarbon stream by the catalyst to form a resultant hydrocarbon stream containing a reduced amount of the sulfur species relative to the amount initially present in the hydrocarbon feedstream.

For purposes of the present invention, the catalysts suitable for this purpose include a metal oxide, preferably selected from the group consisting of cobalt oxide, molybdenum oxide, nickel oxide, zinc oxide and copper oxide, as well as mixtures of cobalt oxide, molybdenum oxide, nickel oxide, zinc oxide and copper oxide. Preferred catalysts include metal oxides selected from the group consisting of a mixture of cobalt and molybdenum oxides, a mixture of nickel and molybdenum oxides and nickel oxide. Preferably, the catalyst includes at least about 10% total weight of the catalyst of the metal oxide.

The olefins processed in accordance with the present invention preferably include members selected from the group consisting of ethylene, propylene, and butylenes, and mixtures of these olefins with ethane, propane and butanes; most preferably, the hydrocarbon stream includes a mixture of propylene and propane.

The sulfur species present in the olefin feedstream processed in accordance with the present invention may be selected from the group consisting of organic sulfides, disulfides, and mercaptans. The mercaptans are selected from the group consisting of methyl mercaptan, ethyl mercaptan, and propyl mercaptan. The organic sulfides may be selected from the group consisting of methyl sulfides, ethyl sulfides and propyl sulfides and mixtures thereof. The disulfide may be selected from the group consisting of dimethyl disulfide, diethyl disulfide, dipropyl disulfide, methyl ethyl disulfide, methyl propyl disulfide, and ethyl propyl disulfides, and mixtures thereof, such as mixtures of dimethyl disulfide, diethyl disulfide, dipropyl disulfide, methyl ethyl disulfide, methyl propyl disulfide, and ethyl propyl disulfides.

The hydrocarbon stream processed in accordance with the present invention may include an amount up to about 100 wppm of the sulfur species, and typically within the range of about 5 wppm-100 wppm, but more typically within the range of about 5 ppm-50 ppm.

The process for adsorbing sulfur species selected from the group consisting of mercaptans, organic sulfides, and disulfides from olefin hydrocarbon streams in accordance with the present invention is conducted in the absence of extraneously added hydrogen under conditions suitable for adsorbing the sulfur species from the hydrocarbon stream which include a temperature within the range of about 50° C. to about 150° C., and preferably within the range of about 50° C. to about 100° C.; a pressure within the range of about 0 psig to about 2000 psig, and preferably within the range of about 150 psig to about 1100 psig; and a liquid hourly space velocity within the range of about 0.1 v/v/h to about 30 v/v/h, and preferably within the range of about 0.5 v/v/h to about 10 v/v/h. Most preferably the process in accordance with the present invention is performed in the absence of extraneously added hydrogen under conditions which include a temperature of about 75° C., a pressure of about 175 psig, and a liquid hourly space velocity of about 1 v/v/h.

In accordance with the present invention, the reduced amount of sulfur species in the resultant hydrocarbon stream is as low as about 1% relative to the amount initially present in the hydrocarbon feedstream. Preferably greater than about 80% sulfur is removed relative to the initial amount of sulfur present in the hydrocarbon stream prior to being treated in accordance with the adsorption process of the present invention.

DETAILED DESCRIPTION

In the present invention, metal oxides are used to adsorb sulfur from a propylene/propane stream without using hydrogen so as to minimize the decomposition of the catalyst species and hydrogenation of the propylene to undesirable propane.

Figure 1:
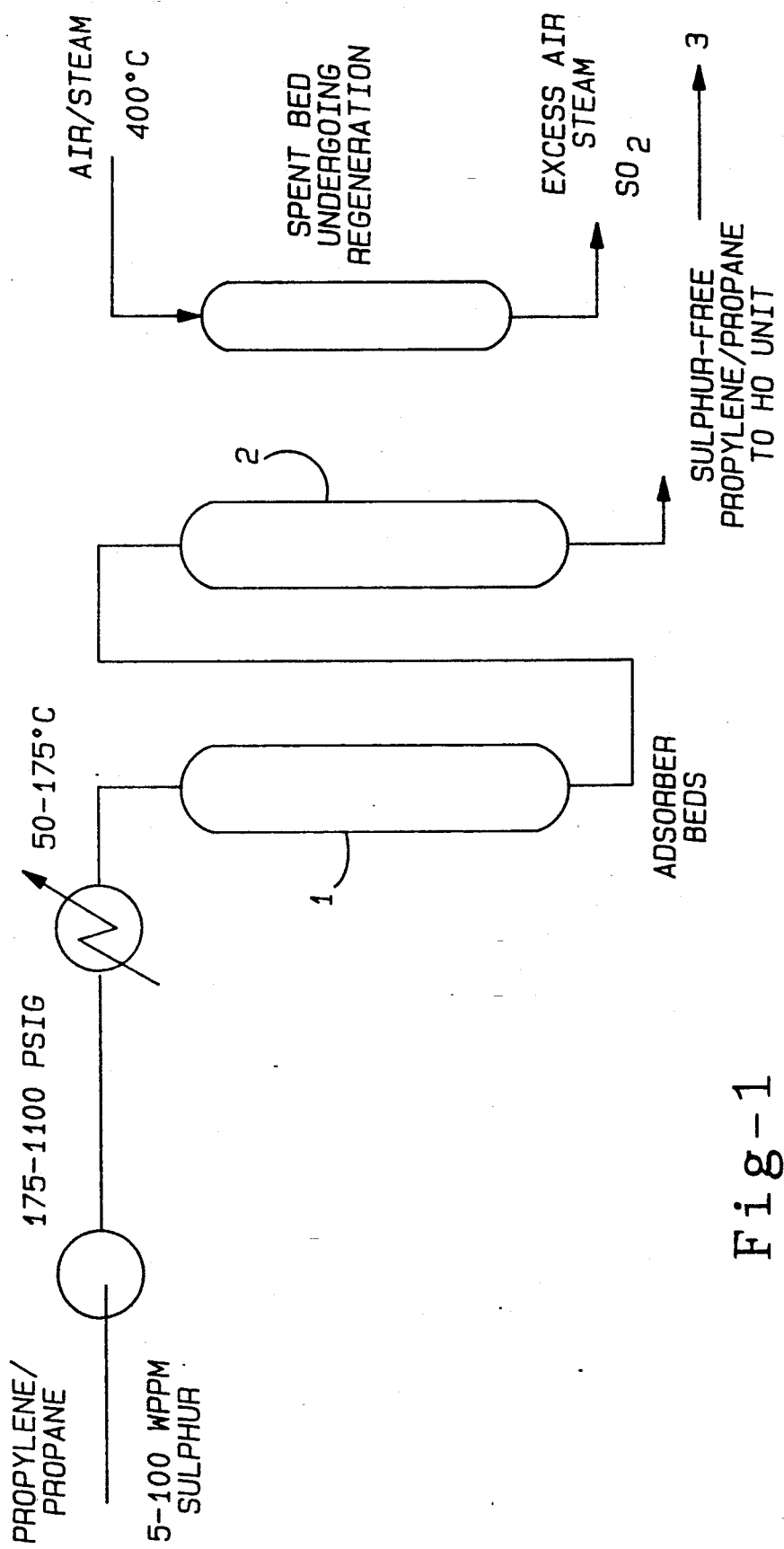
FIG. 1 is a flow chart showing a process for removing sulfur from propylene/propane containing an initial amount of sulfur within the range of 5 wppm-100 wppm in accordance with the present invention wherein the adsorption process is conducted at a temperature within the range of about 50° C.-175° C., and a pressure within the range of 175 psig-1100 psig, to produce a resultant product stream of propylene/propane which is substantially sulfur-free.
Figure 2:
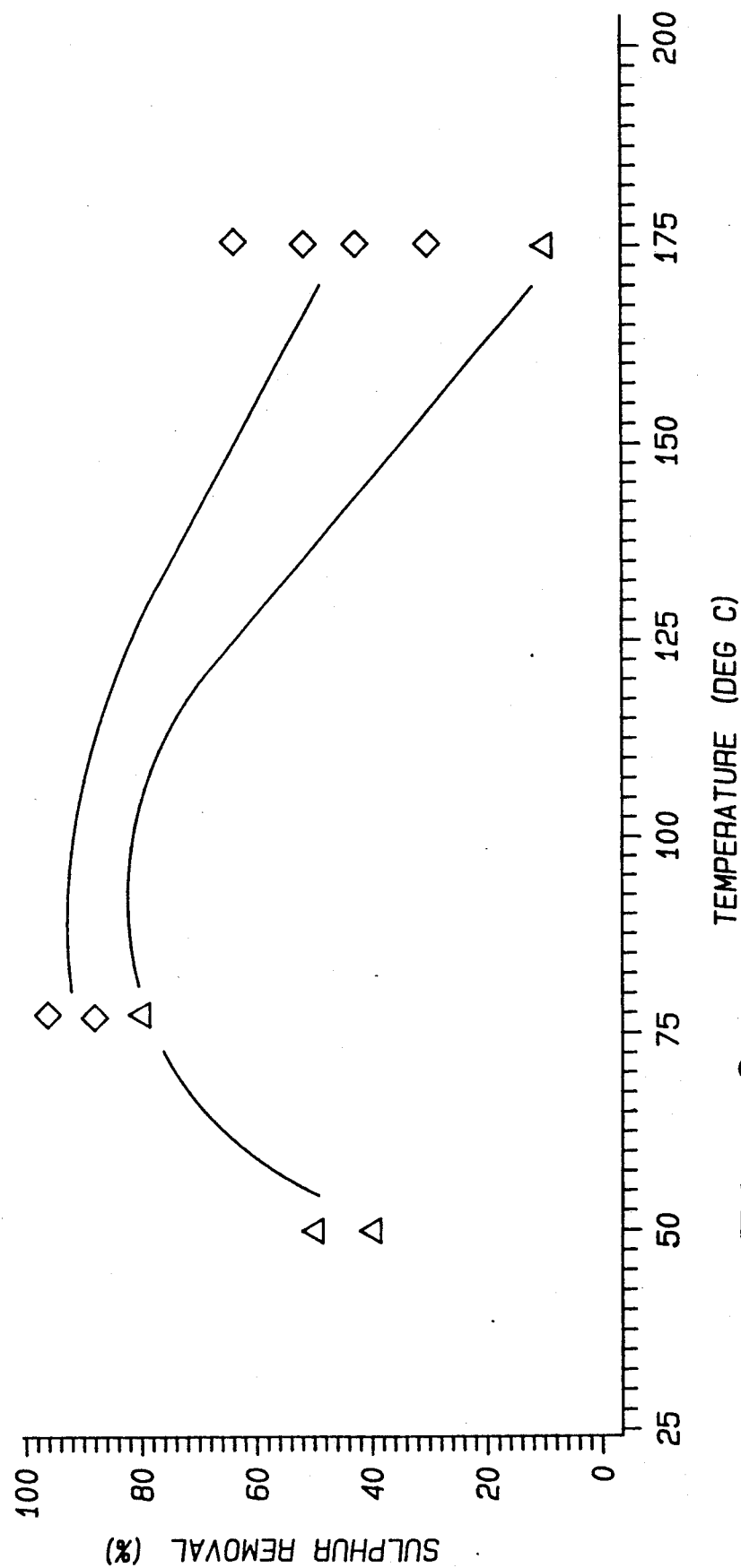
FIG. 2 is a graph showing sulfur removal from propylene/ propane streams wherein the catalytic adsorption process in accordance with the present invention has been performed at a temperature within the range of about 75° C.-130° C., and at liquid hourly space velocities within the range of about 1 v/v/h and 4 v/v/h.

Referring to FIG. 1, adsorbent particles, either unsupported metal oxides or metal oxides on an inert support, are provided in adsorbent beds 1 and 2. An olefin hydrocarbon stream, such as propylene/propane containing 5 wppm-100 wppm of sulfur, is heated to a temperature within the range of about 50° C. to 175° C. and passed at a pressure within the range of about 175 psig-1100 psig and a liquid hourly space velocity of 0.5 v/v/h-10 v/v/h through the adsorbent beds. Subsequently, the substantially sulfur-free propylene/propane resultant stream is fed into a conventional higher olefin process, generally designated as 3.

A preferred higher olefin process useful for purposes of the present invention is disclosed in U.S. Pat. No. 4,675,463, the disclosure of which is hereby incorporated in its entirety by reference thereto herein.

In the conventional higher olefins process, the selected lower olefin is reacted over a solid phosphoric acid catalyst to produce branched mono-olefins of a higher carbon number. These mono-olefins so produced are used as feedstock for hydroformylation to form oxo-aldehydes (which can be subsequently hydrogenated to the corresponding oxo-alcohols and used as intermediates to form phthalate plasticizers, and which can also be employed as detergent intermediates, such as nonyl phenol and dodecyl benzene). The lower olefins which can be used comprise propylene, butenes and pentenes, or mixtures thereof. For example, propylene and butenes from steam cracking and catalytic petroleum cracking are suitable mixtures. Any of the isomeric olefins can be used, alone or as mixtures.

The olefin feedstock is typically first treated to remove deleterious quantities of impurities such as organic sulfur, and diolefins e.g., hydrogen sulfide, mercaptans, methylacetylene, propadiene. Such a feedstock pretreatment can conventionally involve absorption of the impurities with mono- or diethanolamine and caustic wash stages for sulfur removal followed by selective catalytic hydrogenation to reduce the diolefins and acetylenes content.

In addition to the olefins, paraffins and water are also generally introduced. The paraffins comprise propane, butane, and pentane, with the selected paraffin generally comprising a molecule of the same molecular structure as the selected olefin, e.g., propane for propylene feeds, butane for butylene feeds, and the like. The function of the propane is as a diluent of the olefin feed to prevent excessive catalyst temperatures from being achieved within the reactor, and thereby control undesired exotherms. In addition, water is typically employed in the olefin feed, and the water content is maintained at a level which is selected to control the hydration level of the phosphoric acid catalyst. Such a hydration level control is important to maintain activity and life of the phosphoric acid catalyst. Typically, olefin feeds to such an oligomerization reactor will comprise from about 20 wt. % to 60 wt. % olefin, from about 40 wt. % to 80 wt. % paraffin, and from about 0.01 wt. % to 0.07 wt. % water, and more typically from about 30 wt. % to 40 wt. % olefin, from about 60 wt. % to 70 wt. % paraffin, and from about 0.02 wt. % to 0.04 wt. % water. However, the quantity of paraffin and water, and amounts of olefin, can vary widely depending on the olefin selected, the temperature and pressures to be employed in the oligomerization reactor, the precise products which are sought to be formed, the type of reactor which is employed and other factors.

Generally, the oligomerization reaction is conducted at a temperature of from about 150° C. to 230° C., more typically from about 165° C. to 215° C., and at a pressure of from about 4100 kPA to about 8200 kPa, more typically from about 4800 kPa to about 7000 kPa. Again, the precise temperature and pressure employed in the olefin oligomerization reactor will depend on a large number of factors, among them the type of olefin which is fed, the olefin distribution of products which is sought to be formed, and other factors.

The olefins can be passed to the reactor in either the liquid or vapor form, and feed rates are generally in the range of from about 1 to about 3.5 L/kg.h typically from about 2 to about 3 L/kg.h.

Since the oligomerization is exothermic, the desired reaction temperature is conventionally maintained either by quenching with the selected paraffin gas, as by quenching between the catalyst stages when the reactor includes a multi-stage vessel containing catalysts, or by conducting the reaction in a tubular reactor in which the phosphoric acid is contained within a plurality of parallel arranged tubes and around which cooling water is circulated for steam generation in order to remove the desired quantity of heat.

The phosphoric acid catalyst is conventional and can comprise phosphoric acid on silica gel or of other materials of a silicous character, including diatomacous earth, kieselguhr and the like. Such conventional phosphoric acid catalysts are disclosed in U.S. Pat. Nos. 2,586,852 and 2,713,560, the disclosures of which are hereby incorporated herein in their entities by reference thereto.

EXAMPLE I

A propylene/propane stream containing about 40 wppm sulfur, composed of about 30 wppm sulfur from methyl ethyl sulfide, 7 wppm sulfur from diethyl sulfide and 3 wppm sulfur from various other sulfur species, was processed in accordance with the present invention, as shown in FIG. 1, by passing the higher olefin hydrocarbon stream containing the sulfur species through the catalyst beds packed with a commercial CoMo oxide catalyst, i.e., 4% CoO and 15% $MoO_3$, in the absence of extraneously added hydrogen at a temperature of 75° C., a pressure of 175 psig and a liquid hourly space velocities of 1 v/v/h. Under such conditions, sulfur removals of greater than 80% and as high as at least 95% relative to the initial amount of the sulfur species present in the feedstream were obtained.

EXAMPLE II

The process of the present invention, as shown in FIG. 1, was repeated for a number of propylene/propane higher olefin hydrocarbon feedstreams containing sulfur species in about the same proportions as in Example I, present at about 16 wppm and at about 40 wppm at conditions specified below in the absence of extraneously added hydrogen. The results of such runs are tabulated below:

TABLE 1

SULFUR REMOVAL FROM PROPYLENE/PROPANE
CATALYST: Cyanamide HDS 20 COMO

| Run # | Feed Sulfur (wppm) | Temperature (°C.) | Pressure (psig) | Space Velocity (v/v/h) | Product Sulfur (wppm) | Sulfur Removal % |
|---|---|---|---|---|---|---|
| 1 | 40 | 50 | 710 | 4.0 | 20 | 50 |
| 2 | 40 | 50 | 705 | 3.8 | 24 | 40 |
| 3 | 40 | 175 | 705 | 1.0 | 25 | 38 |
| 4 | 40 | 75 | 175 | 1.0 | 2 | 95 |
| 5 | 40 | 75 | 715 | 4.0 | 60 | — |
| 6 | 16 | 175 | 180 | 4.2 | 14 | 12 |
| 7 | 16 | 175 | 710 | 1.1 | 7 | 56 |
| 8 | 16 | 75 | 700 | 4.0 | 3 | 81 |

EXAMPLE III

The process of the present invention, as shown in FIG. 1, was again repeated for a number of propylene/propane higher olefin hydrocarbon streams containing an initial amount of sulfur species in about the same proportions as in Example I at conditions specified below, in the absence of extraneously added sulfur. The results are tabulated below.

TABLE 2

SULFUR REMOVAL FROM PROPYLENE/PROPANE OVER
VARIOUS METAL OXIDE CATALYSTS

| Run # | Feed Sulfur wppm | Temperature (°C.) | Pressure (psig) | LHSV (v/v/h) | Sulfur Removal | | | |
|---|---|---|---|---|---|---|---|---|
| | | | | | CoMo | NiMo | Ni | Support |
| 1. | 16–40 | 75 | 175 | 1 | 90–95 | >95 | >90 | <10 |
| 2. | 15–40 | 75 | 700 | 4 | 0 | >90 | 0 | — (1) |
| | | | | | 80 | — | 80 | <10 (2) |
| 3. | 13–19 | 175 | 175 | 4 | <10 | <10 | <10 | — |
| 4. | 13–40 | 175 | 700 | 1 | 30–55, 50–60 | <10 | <10 | <10 |

(1) When run immediately after condition 1. in the run sequence.
(2) When run immediately after condition 4. in the run sequence.

In accordance with the present invention, the metal sulfide catalyst may be subsequently regenerable using a mixture of air and steam at 400° C. The regeneration removes coke from the catalyst surface and re-oxidizes metal sulfides to the corresponding metal oxides. Thus, spent or deactivated adsorbent used to remove the sulfur species from the higher olefin stream, as described above, may be regenerated in situ or the deactivated adsorbent may be removed and regenerated off-site using conventional techniques. As should be apparent from what is illustrated in FIG. 1, the vessel from the lead position in a series can undergo regeneration while the remaining vessels continue to operate. The regenerated bed will then be returned to service as the last vessel in the series.

Substantial regeneration of spent absorbent can be achieved with the following procedure:

The spent adsorbent bed is purged with a sulfur-free and hydrogen-free inert gas such as $N_2$, steam, methane, and the like prior to heating the bed to about 200° C. and holding at that temperature for at least 45 min. while continuing inert gas purge. The bed is then cooled to operating temperature while continuing inert gas purge.

Periodically, a more severe regeneration may be required to recover the small portion of capacity lost during the above regeneration. The more severe regeneration involves a reoxidation of the catalyst with air at high temperature. Thus, the bed is purged with air or a mixture of air and an inert gas such as nitrogen or steam so that the purge gas contains 1-20% oxygen, then heating the bed to 400° C.-500° C. The flow of purge gas is then continued at this temperature for 4-72 hrs., until all signs of oxidation are gone. Finally, the bed is cooled and the adsorption mode is restarted.

Although the invention has been described with reference to particular means, materials and embodiments, it should be noted that the invention is not limited to the particulars disclosed, and that the foregoing descriptions that are preferred embodiments of the invention. Thus, the present invention is not limited to the particulars disclosed but extends to all equivalents, and various changes and modifications may be made in the invention without departing from the spirit and scope thereof.

What is claimed is:

1. A method of removing sulfur components from a hydrocarbon stream consisting essentially of olefins, said method:

contacting a hydrocarbon stream consisting essentially of olefins selected from the group consisting of ethylene, propylene, butene, mixtures of ethylene, propylene, and butene, and mixtures of ethylene, propylene, butene, with ethane, propane, and butane, and an initial amount of at least one sulfur species selected from the group consisting of mercaptans, organic sulfides, and disulfides with a catalyst capable of adsorbing said sulfur species in the absence of extraneously added hydrogen at a temperature within the range of about 50° C. to about 75° C. and under conditions suitable for removing said at least one sulfur species from said hydrocarbon stream comprising said olefins by said catalyst to form a resultant hydrocarbon stream consisting essentially of said olefins containing a reduced amount of said at least one sulfur species.

2. The method of removing sulfur components from a hydrocarbon stream consisting essentially of olefins as defined by claim 1, wherein said catalyst comprises a metal oxide.

3. The method of removing sulfur components from a hydrocarbon stream consisting essentially of olefins as defined by claim 2, wherein said metal oxide is selected from the group consisting of cobalt oxide, nickel oxide, molybdenum oxide, zinc oxide and copper oxide and mixtures of at least two members selected from the group consisting of cobalt oxide, nickel oxide, molybdenum oxide, zinc oxide and copper oxide.

4. The method of removing sulfur components from a hydrocarbon stream consisting essentially of olefins as defined by claim 3, wherein said metal oxide is selected from the group consisting of cobalt oxide, nickel oxide, a mixture of cobalt and molybdenum oxides, and a mixture of nickel and molybdenum oxides.

5. The method of removing sulfur components from a hydrocarbon stream consisting essentially of olefins as defined by claim 4, wherein said catalyst comprises at least 10% by total weight of said metal oxide.

6. The method of removing sulfur components from a hydrocarbon stream consisting essentially of olefins as defined by claim 3, wherein said catalyst comprises said metal oxide in the form of particles on a support.

7. The method of removing sulfur components from a hydrocarbon stream consisting essentially of olefins as defined by claim 5, wherein said support is an inert support.

8. The method of removing sulfur components from a hydrocarbon stream consisting essentially of olefins as defined by claim 7, wherein said inert support is a member selected from the group consisting of alumina, silica and clay.

9. The method of removing sulfur components from a hydrocarbon stream consisting essentially of olefins as defined by claim 8, wherein said support is alumina.

10. The method of removing sulfur components from a hydrocarbon stream consisting essentially of olefins as defined by claim 1, wherein said olefins consists essentially of propylene.

11. The method of removing sulfur components from a hydrocarbon stream consisting essentially of olefins as defined by claim 10, wherein said olefins consists essentially of a mixture of propylene and propane.

12. The method of removing sulfur components from a hydrocarbon stream consisting essentially of olefins as defined by claim 1, wherein said olefins consists essentially of an initial amount up to about 100 wppm of said at least one sulfur species.

13. The method of removing sulfur components from a hydrocarbon stream consisting essentially of olefins as defined by claim 12, wherein said initial amount of said at least one sulfur species is within the range of about 5 wppm-100 wppm.

14. The method of removing sulfur components from a hydrocarbon stream consisting essentially of olefins as defined by claim 13, wherein said initial amount of said at least one sulfur species is within the range of about 5 wppm-50 wppm.

15. The method of removing sulfur components from a hydrocarbon stream consisting essentially of olefins as defined by claim 1, wherein said at least one sulfur species is selected from the group consisting of organic sulfides and mercaptans.

16. The method of removing contaminants from a hydrocarbon stream consisting essentially of olefins as defined by claim 15, wherein said at least one sulfur species is selected from the group consisting of organic sulfides.

17. The method of removing contaminants from a hydrocarbon stream consisting essentially of olefins as defined by claim 16, wherein said organic sulfides are selected from the group consisting of methyl sulfides, ethyl sulfides, and propyl sulfides, and mixtures of methyl sulfides, ethyl sulfides and propyl sulfides.

18. The method of removing contaminants from a hydrocarbon stream consisting essentially of olefins as defined by claim 15, wherein said at least one sulfur species is selected from the group consisting of mercaptans.

19. The method of removing sulfur components from a hydrocarbon stream consisting essentially of olefins as defined by claim 18, wherein said mercaptans are members selected from the group consisting of methyl-mercaptan, ethyl-mercaptan, propyl mercaptan and butyl mercaptan.

20. The method of removing sulfur components from a hydrocarbon stream consisting essentially of olefins as defined by claim 1, wherein said sulfides are members selected from the group consisting of dimethyl sulfides, methylethyl sulfides, diethyl sulfides, methyl propyl sulfide and ethyl propyl sulfides.

21. The method of removing sulfur components from a hydrocarbon stream consisting essentially of olefins as defined by claim 1, wherein said disulfides are selected from the group consisting of dimethyl disulfide, diethyl disulfide, dipropyl disulfide, methyl ethyl disulfides, methyl propyl disulfides, ethyl propyl disulfides and mixtures thereof.

22. The method of removing sulfur components from a hydrocarbon stream consisting essentially of olefins as defined by claim 1, wherein said conditions suitable for adsorbing said at least one sulfur species comprise a pressure within the range of about 0 psig to about 2000 psig.

23. The method of removing sulfur components from a hydrocarbon stream consisting essentially of olefins as defined by claim 22, wherein said pressure is within the range of about 150 psig to about 1100 psig.

24. The method of removing sulfur components from a hydrocarbon stream consisting essentially of olefins as defined by claim 1, wherein said conditions suitable for adsorbing said at least one sulfur species comprise a liquid hourly space velocity within the range of 0.1 v/v/h to about 30 v/v/h.

25. The method of removing sulfur components from a hydrocarbon stream consisting essentially of olefins as defined by claim 24, wherein said liquid hourly space velocity is within the range of about 0.5 v/v/h to about 10 v/v/h.

26. The method of removing sulfur components from a hydrocarbon stream consisting essentially of olefins as defined by claim 1, wherein said reduced amount of said at least one sulfur species in said resultant olefin stream is within the range of less than about 20% by weight of the initial amount present in said hydrocarbon stream.

27. The method of removing sulfur components from a hydrocarbon stream consisting essentially of olefins as defined by claim 26, wherein said conditions comprise a temperature of about 75° C.; a pressure of about 175 psig; and a liquid hourly space velocity of about 1 v/v/h.

28. The method of removing sulfur components from a hydrocarbon stream consisting essentially of olefins as defined by claim 27, wherein said reduced amount of said at least one sulfur species present in said resultant olefin stream is within the range of less than about 10% by weight of the initial amount present in said hydrocarbon stream.

29. The method of removing sulfur components from a hydrocarbon stream consisting essentially of olefins as defined by claim 28, wherein said catalyst is selected from the group consisting of a mixture of cobalt and molybdenum oxides, a mixture of nickel and molybdenum oxides and nickel oxide.

30. The method of removing sulfur components from a hydrocarbon stream consisting essentially of olefins as defined by claim 4, wherein said catalyst comprises metal oxides selected from the group consisting of a mixture of cobalt and molybdenum oxides.

* * * * *